United States Patent [19]

Soled et al.

[11] Patent Number: 4,670,476
[45] Date of Patent: Jun. 2, 1987

[54] MANGANESE-SPINEL CATALYSTS IN CO/H₂ OLEFIN SYNTHESIS

[75] Inventors: Stuart L. Soled, Madison; Rocco A. Fiato, Scotch Plains, both of N.J.

[73] Assignee: Exxon Research and Engineering Company, Florham Park, N.J.

[21] Appl. No.: 817,778

[22] Filed: Jan. 8, 1986

Related U.S. Application Data

[63] Continuation of Ser. No. 564,464, Dec. 20, 1983, abandoned.

[51] Int. Cl.⁴ .................................................. C07C 1/04
[52] U.S. Cl. ..................................... 518/717; 518/721; 518/720; 502/241
[58] Field of Search ............... 518/717, 719, 720, 721

[56] References Cited

U.S. PATENT DOCUMENTS

| | | | |
|---|---|---|---|
| 2,605,275 | 10/1948 | Kearby et al. | 260/449.6 |
| 2,778,845 | 1/1957 | McGrath et al. | 260/449.6 |
| 2,846,488 | 8/1958 | Miller | 260/667 |
| 4,177,203 | 12/1979 | Kolbel et al. | 260/449.6 R |
| 4,186,112 | 1/1980 | Vogt et al. | 252/471 |

FOREIGN PATENT DOCUMENTS

| | | |
|---|---|---|
| 71770 | 2/1983 | European Pat. Off. |
| 816884 | 10/1981 | South Africa |

OTHER PUBLICATIONS

"Iron/Manganese Oxide Catalysts for Fischer-Tropsch Synthesis, Part I: Structural and Textural Changes by Calcination, Reduction and Synthesis" Applied Catalysis, vol. 5 (1983) pp. 151 to 170 by G. C. Maiti et al.
"Effects of Managanese Oxide and Sulphate on the Olefin Selectivity of Iron Catalysts in the Fischer Tropsch Reaction" Applied Catalysis, vol. 2, (1982) pp. 273 to 288 by W. L. van Dijk et al.
73rd AIChe Meeting, Paper #103D by H. J. Lehman and M. Rollick "Development of a New Type of Catalysts for the Selektive Fischer-Tropsch Synthesis".
"Make Olefins From Syn Gas", Hydrocarbon Processing, Nov. 1980, pp. 139 to 142, by V. Rao and R. Gormley.
"Unconventional Olefin Processes" Hydrocarbon Processing, May 1983, pp. 88-96 by Y. C. Hu.
"The Synthesis of Hydrocarbons and Oxygen-Containing Compounds From Carbon Monoxide and Hydrogen Over Iron-Copper Catalysts", Khimiya i. Tekhnologiya Topliv i Masel, No. 6, pp. 5 to 10, June 1965 (Russian).
"Feedstock for Chemical Industry by Selective Fischer-Tropsch Synthese" by H. Kolbel et al., II 1978 Society of Automotive Engineers, pp. 482–486.
"Light Olefin Production from CO/Hydrogen over Silica Supported Iron/Manganese/Potassium Catalysts Derived from a Bi-Metalic Carbonyl Anion, [Fe₂Mn(CO)₁₂]⁻pp. 175–180 (1982).
Prace Ustavu Vyzkum Paliv. 8, pp. 39–81 (1964) (Czech.).
Khim. i Tekhnol. Topliv i Masel 10 (6), 5–10 (1965).
Intersoc. Energy Convers. Eng. Conf. 1978, 13(1) 482–486 (Eng.).
Chem.-Ing.-Tech. 1981, 53(10) 818–819.
Hydrocarbon Process, V. 59, No. 11, 139–142 (Nov. 1980).
Appl. Catal. 1982, 2(4–5), 273–288.
React. Kinet. Catal. Lett. (1982) 20(1–2) 175–180.
73rd AIChe Ann. Meet. Pap. N. 103D.

*Primary Examiner*—Howard T. Mars
*Attorney, Agent, or Firm*—Edward M. Corcoran

[57] ABSTRACT

Single phase, unsupported, Group IA or IIA metal salt promoted manganese-containing iron spinel catalysts, having Fe:Mn atomic ratios of 2:1 or above, have been found to be highly active for the selective conversion of CO/H₂ to alpha olefins.

15 Claims, No Drawings

MANGANESE-SPINEL CATALYSTS IN CO/H$_2$ OLEFIN SYNTHESIS

This application is a continuation, of application Ser. No. 564,464, filed Dec. 20, 1983, now abandoned.

BACKGROUND OF THE INVENTION

1. Field of the Invention

This invention relates to a Fischer-Tropsch process for selectivity producing low molecular weight alpha-olefins utilizing an unsupported single phase Fe-Mn spinel catalyst promoted with Group IA or IIA metal salt in which the atomic ratio of Fe:Mn is 2:1 or above.

2. Brief Description of the Prior Art

Fischer-Tropsch processes have long been known to produce gaseous and liquid hydrocarbons containing $C_2$–$C_4$ olefins. Because of the importance of $C_2$–$C_4$ olefins, particularly as feedstocks for the chemical industry, modifications of the Fischer-Tropsch process are constantly being pursued toward the goals of maximizing $C_2$–$C_4$ olefin selectivity with the particular objective of maintaining high catalyst activity and stability under the reaction conditions. The main thrust of the efforts in this area has been in the area of catalyst formulation.

Coprecipitated and/or supported iron-based catalysts, including those containing manganese, are known for producing $C_2$–$C_4$ olefins. Examples of disclosures in the art directed to such iron-manganese catalysts and/or alloys include: W. L. vanDijk, et al., *Appl. Catal.*, 2, 273 (1982); Eur. Pat. Appl. 49888 to Ruhrchemie (1981); H. J. Lehman, 73rd AIChe Meeting Paper #103D; W. D. Deckwer, et al., *Chem. Ing. Tech.*, 53 (10) 818 (1981); V. Rao and R. Gormley, *Hydrocarbon Processing*, 139, November (1981); H. Kolbel and K. Tillmetz, U.S. Pat. No. 4,177,203 (1970); EPO Patent Publication No. 0,071,770; U.S. Pat. No. 2,605,275; U.S. Pat. No. 2,850,515; *Prepr. Div. Pet. Chem. Am. Chem. Soc.* (1978) 23(2) pp 513–20; *Intersoc. Energy Convers. Eng. Conf.* 1978, 13(1) pp 482–6; U.S. Pat. No. 4,186,112; EP 49,888; React Kinet. Catal. Lett. 1982, 20(1-2) pp 175–80; U.S. Pat. No. 2,778,845; *Khim.* (1) *Tekhnol. Topliv i Masel* (Russ.) 10(6) 5–10 (1965); UK Patent Appln. No. 2,050,859 A; German Patent Appln. No. OT 2919-921; *Prace Ustavu Vyzkum Paliv* 8, p. 39–81 (1964) (Czech).

An iron-manganese spinel of the formula, Fe$_2$MnO$_4$, is reported as a catalyst component formed during Fischer-Tropsch synthesis in which a coprecipitated Fe/Mn oxide catalyst is initially employed in *Applied Catalysis* 5 (1983) pp. 151–170. However, this and the above cited references do not describe a Fischer-Tropsch hydrocarbon process initially employing an unsupported single phase Fe/Mn spinel catalyst having an Fe:Mn atomic ratio of 2:1 or above and being promoted with a Group IA or IIA metal salt promoter agent.

What is particularly desired in fixed bed Fischer-Tropsch processes are catalysts for selectively producing high levels of $C_2$–$C_4$ olefins and low levels of methane under the desirable combined conditions of high catalyst activity and stability.

SUMMARY OF THE INVENTION

It has been found that unsupported single phase iron-manganese spinels containing iron:manganese atomic ratios of 2:1 or above and being preferably promoted with a Group IA or IIA metal salt, preferably being substantially deposited on the surface of said spinel provide desirable catalyst properties in fixed bed Fischer-Tropsch processes. The initial spinels prior to reduction and carbiding exhibit an X-ray diffraction pattern isostructural with Fe$_3$O$_4$.

The subject spinels are prepared in a high temperature solid state sintering reaction in a temperature range of about 600° to 1100° C. between the component metal oxides and/or metals and mixtures thereof, in an inert oxygen-free atmosphere or under vacuum. The spinels prepared in this manner can then be treated by surface impregnation or deposition with promoter agents, particularly Group IA and Group IIA metal salts, and particularly, potassium carbonate and potassium sulfate. The resulting iron/potassium atomic ratio is desirably in the range of about 20:1 to 200:1. The promoted catalyst can then be partially reduced by contacting with a hydrogen containing gas and partially carbided in a CO-containing atmosphere before use in the Fischer-Tropsch process. By the terms "partially reduced" and "partially carbided" is meant that the iron "portion" of the spinel is substantially reduced and carbided and that the manganese portion of the spinel remains substantially as the oxide.

In accordance with this invention there is provided a hydrocarbon synthesis catalyst composition comprising an unsupported Group IA or IIA metal salt promoted iron-manganese single phase spinel, said spinel having the initial empirical formula:

$$Fe_xMn_yO_4$$

wherein x and y are integer or decimal values, other than zero, with the proviso that the sum of x+y is 3 and the ratio of x/y is 2:1 or above, said spinel exhibiting a powder X-ray diffraction pattern substantially isostructural with Fe$_3$O$_4$ and said metal salt being substantially deposited on the surface of said spinel.

Preferred embodiments of the composition include the partially reduced and carbided form of the spinel, which is an active Fischer-Tropsch catalyst in fixed bed process for producing low molecular weight olefins.

Furthermore, there is provided a process for producing the above-described spinel portion of the composition comprising heating a mixture of iron and manganese as their oxides and/or free metals at elevated temperature in an oxygen free or inert atmosphere for a sufficient time until the resulting oxide mixture exhibits an X-ray diffraction pattern isostructural with Fe$_3$O$_4$.

There is further provided a process for synthesizing a hydrocarbon mixture containing $C_2$–$C_6$ olefins comprising the step of contacting a catalyst composition comprised of an unsupported Group IA or IIA metal salt promoted iron-manganese spinel; said spinel initially exhibiting a single spinel phase, being isostructural with Fe$_3$O$_4$ as determined by X-ray diffractometry, and possessing an iron-manganese atomic ratio of 2:1 or above with a mixture of CO/hydrogen under process conditions of pressure, space velocity (SHSV) and elevated temperature for a time sufficient to produce said $C_2$–$C_6$ olefins.

Also provided is a process for synthesizing a hydrocarbon mixture containing $C_2$–$C_6$ olefins comprising the step of contacting a partially reduced and carbided catalyst composition comprised of an iron-manganese spinel of the formula: Fe$_2$MnO$_4$/1 gram-atom % K, as K$_2$SO$_4$, said spinel initially exhibiting a single spinel phase, being isostructural with $Fe_3O_4$ as determined by X-ray diffractometry, with a 1:1 mixture of CO/hydrogen under process conditions of 300 psig pressure, 1000 v/v/hr. space velocity (SHSV) and 300° C. temperature for time sufficient to produce said $C_2$–$C_6$ olefins.

DESCRIPTION OF THE INVENTION AND PREFERRED EMBODIMENTS

The subject unsupported alkali- or alkaline earth metal salt promoted iron-manganese single phase spinels are new compositions of matter which are isostructural with $Fe_3O_4$, as determined by x-ray diffractometry using copper K alpha radiation and exhibit a single spinel phase. By the term "spinel" is meant a crystal structure whose general stoichiometry corresponds to $AB_2O_4$, where A and B can be the same or different cations. Included within this definition is the commonly found spinel, $MgAl_2O_4$, A and B can have the following cationic charge combinations: $A=+2$, $B=+3$, $A=+4$, $B=+2$, or $A=+6$, $B=+1$. Spinels contain an approximately cubic close-packed arrangement of oxygen atoms with $\frac{1}{8}$th of the available tetrahedral interstices and $\frac{1}{2}$ of the octahedral interstices filled, and can exhibit hundreds of different phases. Further description of the spinel structure can be found in "Structural Inorganic Chemistry" by A. F. Wells, Third Edition, Oxford Press, and the Article "Crystal Chemistry and Some Magnetic Properties of Mixed Metal Oxides with the Spinel Structure" by G. Blasse, Phillips Research Review Supplement, Volume 3, pp 1–30, (1964). By the term "isostructural" is meant crystallizing in the same general structure type such that the arrangement of the atoms remains very similar with only minor change in unit cell constants, bond energies and angles. By the term "single phase spinel", as used herein, is meant one structural and compositional formula, corresponding to a single spinel material into which all of the metal components are incorporated, and exhibiting one characteristic X-ray diffraction pattern.

The subject iron-manganese spinels generally possesses a BET surface area up to about 5 $m^2/g$, as determined by the well-known BET surface area measurement technique as described in the reference JACS 60, p.309 (1938) by S. Brunauer, P. H. Emmett, and G. Teller. Preferably, the spinel has a surface area of about 0.1 to 5 $m^2/g$. This range of surface area generally corresponds to a particle size range of about 1 to 10 microns.

The spinel can be represented by the formula: $Fe_xMn_yO_4$, wherein x and y are decimal or integer values, other than zero, and wherein the sum of x plus y is 3, and the ratio of x to y is greater than 2:1 or above, and preferably being about 2:1 to 19:1 and particularly preferred is where the iron to manganese atomic ratio is about 3:1 to 7:1. The composition can further be comprised of a mixture of single phase spinels, of different iron-manganese atomic ratios.

Representative examples of the various spinels corresponding to the formula are $Fe_{2.85}Mn_{0.15}O_4$, $Fe_{2.625}Mn_{0.375}O_4$, $Fe_{2.25}Mn_{0.75}O_4$, $Fe_{2.97}Mn_{0.03}O_4$.

Physical properties in general of these subject spinels are similar to those of magnetite and include melting point of above 1400° C., and a color of brownish-red.

The iron-manganese spinels are used in unsupported form in $H_2$/CO hydrocarbon synthesis.

A Group IA alkali metal or Group IIA alkaline earth metal salt promoter agent is used in the subject composition and can also be used to particularly promote olefin formation in the subject process. Representative examples of suitable classes of promoter agents include carbonates, bicarbonates, organic acid and inorganic acid salts e.g. acetates, nitrates, halides, sulfates, and hydroxide salts of Group IA and IIA metals including lithium, sodium, potassium, cesium, rubidium, barium, strontium, magnesium and the like.

Representative examples of specific promoter agents are potassium carbonate, potassium sulfate, potassium bicarbonate, cesium chloride, rubidium nitrate, lithium acetate, potassium hydroxide, and the like. Preferred are the Group IA compounds and a particularly preferred promoter agent is potassium carbonate. The promoter, if used, is generally present in about a 0.1 to 10 gram-atom % of the total gram-atoms of metals present. A preferred level of promoter agent is in the range of 1 to 2 gram-atom % of the total gram-atom metal present. In the empirical formulas used herein, the amount of the promoter agent, e.g., potassium, is expressed in terms of gram atom percent based on the total gram-atoms of metals used. Thus, "1 gram-atom percent of potassium signifies the presence of 1 gram-atom of potassium per 100 total gram atoms of combined gram atoms of Fe and Mn. Thus, the symbol "/1% K" as used herein indicates 1 gram-atom percent potassium based on each 100 gram atom of the total gram atom of iron and manganese present.

A particularly preferred spinel composition of the subject invention is $Fe_{2.25}Mn_{0.75}O_4$/1% K. The catalyst spinel in the subject process may also be used in conjunction with a diluent material, one which aids in heat transfer and removal from the catalyst bed. Suitable materials include powdered quartz, silicon carbide, powdered borosilicate glass, kieselguhr, zeolites, talc, clays, Group II–VII oxides and rare earth oxides including $TiO_2$, $SiO_2$, $Al_2O_3$, MgO, $La_2O_3$, $CeO_2$, $Cr_2O_3$, $MnO_2$ and the like.

The diluent, if used, is generally used in a 1:4 to 9:1 diluent/spinel composition weight ratio to the spinel. Preferred is a 1:1 weight ratio.

The utility of these spinels is their ability upon subsequent reduction and carbiding to form active catalysts in a fixed bed Fisher-Tropsch process for making $C_2$–$C_6$ olefins from CO/hydrogen.

The partially reduced and carbided forms of the above-described spinel are also subjects of this invention.

The subject spinel is prepared by a solid state high temperature reaction between (1) the component oxides, i.e. $Fe_3O_4$ and $Mn_3O_4$, or (2) a mixture of iron metal, manganese oxide and iron oxide, i.e. Fe, $Mn_3O_4$ and $Fe_2O_3$ or (3) a mixture of manganese metal, iron oxide and manganese oxide, i.e. Mn, $Fe_3O_4$, $Fe_2O_3$ and $Mn_3O_4$, or (4) a mixture of iron and manganese metals, iron oxide and manganese oxide, i.e., Fe, Mn, $Fe_2O_3$ and $Mn_3O_4$, in the empirical formula for the composition formula as given above. Preferred is reaction (2) described above. The reaction is conducted at temperatures in the range of about 600° to 100° C. and preferably from about 800° to 1000° C., in an inert gas, oxygen-free atmosphere or vacuum environment. Example of useful inert gases are helium, nitrogen, argon, and the like. The solid state high temperature reaction "sintering" should be performed on thoroughly mixed samples of the metal oxides and/or metal and metal oxide mixtures. Preferred method of forming the mixture is by intimate grinding. The sintering reaction should be conducted until an X-ray diffraction pattern indicates a single spinel phase is formed which generally requires about an 8 to 24 hour period and preferably about 12 to 18 hour period. Generally, at the end of each reaction period material is thoroughly ground and mixed and then resubjected to the high temperature conditions for an additional 1 to 5 cycles or until X-ray diffraction reveals the presence of a single spinel phase.

Prior to the hydrocarbon synthesis run the iron-manganese spinel is conditioned by treating in a reducing atmosphere at elevated temperature, generally in a temperature range of about 200° to 500° C. and preferably 350° to 450° C. The treatment can be carried out with various reducing gases including hydrogen, hydrogen/CO and the like, and mixtures thereof. Preferably, hydrogen gas, either by itself or in an inert carrier medium such as helium neon, argon, or nitrogen, is preferably used. The pressure of the reducing gas in this procedure may be in the range of 1.5 to 1000 psig and preferably in the range of 15 to 150 psig. The reducing gas feed rate may be in the range of 1–10,000 V/V/hr and preferably in the range of 10–1000 V/V/hr. A preferred method of totally reducing the Fe-Mn spinel is described in copending SN (C-1544), in which the spinel is heated with metallic calcium to substantially form Fe-Mn alloy after acid leaching.

The resulting partially reduced spinel is useful in the subject Fischer-Tropsch process for making $C_2$ to $C_6$ olefins as described herein, after being treated in a suitable carbiding atmosphere.

Suitable carbiding atmospheres include CO, $CO/H_2$ and the like, and the atmosphere during $CO/H_2$ hydrocarbon synthesis conditions described below. Also, the reduction and carbiding steps can be conducted concurrently in $CO/H_2$.

Also, a subject of the instant invention is a Fischer-Tropsch fixed bed process for producing $C_2$–$C_6$ olefins by utilizing the treated iron-manganese spinel, described hereinabove.

Although a fixed bed Fischer-Tropsch process is a preferred mode for operating the process, utilizing the catalysts described herein, a slurry type process wherein the catalyst is suspended in a liquid hydrocarbon can also be utilized.

The subject fixed bed process utilizes the above-described materials as catalyst, as iron-manganese spinel, isostructural with $Fe_3O_4$, and its reduced and carbided forms. The reduced and carbided materials are generally made in situ in the apparatus prior to, and during the carrying out of the hydrocarbon synthesis process. A full discussion of the spinel and reduced form materials, their properties and their preparation are given hereinabove and need not be reiterated.

Prior to the CO/hydrogen hydrocarbon synthesis fixed bed run, the sintered iron-manganese catalyst is generally conditioned in the apparatus by purging with nitrogen to remove reactive oxygen containing gases and then the temperature is increased to the reaction temperature range. Then the system is generally subjected to a hydrogen treatment for several hours. The pressure and space velocity during this conditioning step are not critical and can be utilized in the range which is actually used during actual hydrocarbon synthesis.

Following the reduction step, the CO/hydrogen feedstream is introduced into the apparatus catalyst chamber and the pressure, space velocity, temperature, and hydrogen/CO molar ratio are then adjusted as desired, for hydrocarbon synthesis conditions. Alternately, the reduction and carbiding steps can be carried out concurrently by contacting the promoted spinel with $CO/H_2$ atmosphere at elevated temperature or under hydrocarbon synthesis conditions.

In the process, the hydrogen and CO are used in a molar ratio in the gaseous feedstream of preferably about a 0.5 to 2.5 molar $H_2/CO$ ratio and preferably 1:1 to 2:1 molar ratio. Higher and lower molar ratios may also be used.

The temperature in the process is generally in the region of about 200° to 350° C. and preferably being 250° to 300° C.

The pressure useful in the process is generally conducted in the range of about 50 to 1000 psig and preferably about 100 to 300 psig. Higher pressures can also be used.

The space velocity (SHSV) used in the process is generally about 200 to 4000 volume of gaseous feedstream/per volume of dry catalyst/per hour and is preferably in the range of about 400 to 1200 V/V/hr. Higher and lower space velocities can also be used.

The percent CO conversion obtainable in the subject process while providing substantial quantities of $C_2$–$C_6$ olefins, ranges from about 20 to 98% and preferably above about 30%. Higher and lower ratio percentages of CO conversion may also be utilized.

"Total hydrocarbons" produced in the process is related to the selectivity of percent CO conversion to hydrocarbons, being those hydrocarbons from $C_1$ to about $C_{40}$ inclusive, and is generally about 0 to 50 percent and higher of the total CO converted, and the remainder being converted to $CO_2$.

The percent total $C_2$–$C_6$ hydrocarbons of the total hydrocarbons produced, including olefins and paraffins is generally about 20 to 50 wt. % and preferably about 40 to 50 wt. %. The weight percent of $C_2$–$C_6$ olefins produced of the $C_2$–$C_6$ total hydrocarbons produced is generally about 50 to 90 wt. % and preferably above 60 wt. % of the $C_2$–$C_6$ total hydrocarbons. The olefins produced in the process are substantially alpha-olefins.

The selectivity to methane based on the amount of CO conversion is about 4 to 10 weight percent of total hydrocarbons produced. Preferably about 8 percent and lower methane is produced in the process.

As discussed above the percent selectivity to $CO_2$ formation in the process is about 40 to 50 percent of CO converted.

The reaction process variables are preferably adjusted to minimize $CO_2$ production, minimize methane production, maximize percent CO conversion, and maximize percent $C_2$–$C_6$ olefin selectivity, while achieving activity maintenance in the catalyst system.

Generally, this format can be achieved in a preferred mode of operating the process where the empirical formula of the catalyst used is $Fe_{2.25}Mn_{0.75}O_4$/1% K the pretreatment procedure is conducted at 500° C., 9:1 $H_2/N_2$, 5.5 hrs. 100 psig, 500–750 v/v/hr, the CO/hydrogen molar ratio is 1:1, the temperature is conducted in the range 270°–320° C., at a pressure of 150–300 psig, and space velocity 800–1200 v/v/hr. By carrying out the above process in the stated variable ranges efficient activity maintenance and production of $C_2$–$C_6$ olefins can be achieved.

The effluent gases in the process exiting from the reactor may be recycled if desired to the reactor for further CO/hydrocarbon synthesis.

Methods for collecting the products in the process are known in the art and include distillation, fractional distillation, and the like. Methods for analyzing the product liquid hydrocarbons and gaseous streams are also known in the art and generally include gas chromatography, liquid chromatography, high pressure liquid chromatography and the like.

Apparatus useful in the preferred process is any conventional fixed bed type reactor, being horizontal or vertical, moving bed, and the like. Other apparatus not specifically described herein will be obvious to one skilled in the art from a reading of this disclosure.

The following examples are illustration of the best mode of carrying out the claimed invention as contemplated by us and should not be construed as being limiting on the scope and spirit of the instant invention.

EXAMPLE 1

Catalyst Preparation

Solid solutions of the composition $Fe_{3-y}Mn_yO_4$ (where y varies from 0.025 to 2.85 and x as originally defined equals $3-y$) were prepared by carefully weighing and thoroughly mixing $Mn_3O_4$, $Fe_2O_3$ and Fe powder (reagent quality or better -Alfa Chemicals Co.) according to the stoichiometry:

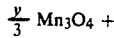
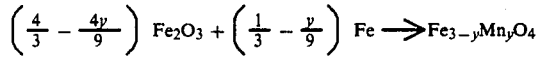

The individual spinels were prepared from the following mixtures of starting materials according to the value of "y" as given below in the Table:

TABLE I

| Catalyst | y | $Fe_2O_3$ (g.) | Fe (g.) | $Mn_3O_4$ (g.) |
|---|---|---|---|---|
| Control | 0 | 21.080 | 1.8400 | 0.00 |
| A | 0.15 | 21.853 | 1.9108 | 1.2360 |
| B | 0.375 | 20.146 | 1.7615 | 3.0927 |
| C | 0.75 | 17.293 | 1.5119 | 6.1946 |
| D | 1.0 | 15.3886 | 1.3379 | 8.2668 |
| E | 1.5 | 23.124 | 2.0221 | 24.849 |
| F | 2.85 | 1.0646 | 0.0931 | 21.737 |

Each solids mixture was placed into a quartz tube (15 mm i.d., 18 mm o.d.) evacuated to $10^{-3}$ torr, sealed under vacuum and then heated to 800° C. for 24 hours. The resulting solids were isolated, thoroughly reground, pelletized and resubjected to the same high temperature sintering process at 800°-1000° C. for an additional 24 to 48 hours. Powder X-ray diffraction analysis was then conducted to ensure that the material was single phase and isostructural with $Fe_3O_4$. The catalyst pellets were then impregnated with aqueous solutions of $K_2CO_3$ or $K_2SO_4$ to achieve a potassium loading level of 1-10 gm atom percent K per gm atom of combined metal, and then dried, pelletized crushed and sieved to 10-40 mesh.

The resulting measured BET nitrogen surface area of each Fe-Mn spinel was measured and the results given below.

TABLE II

| Spinel | Empirical Formula | Surface Area (m²/g) |
|---|---|---|
| Control | $Fe_3O_4$/1% K | 0.27 |
| A | $Fe_{2.85}Mn_{0.15}O_4$/1% K | 0.36 |
| B | $Fe_{2.625}Mn_{0.375}O_4$/1% K | 0.28 |
| C | $Fe_{2.25}Mn_{0.75}O_4$/1% K | 0.21 |
| D | $Fe_2MnO_4$/1% K | 0.25 |

TABLE II-continued

| Spinel | Empirical Formula | Surface Area (m²/g) |
|---|---|---|
| E | $Fe_{1.5}Mn_{1.5}O_4$/1% K | 0.19 |
| F | $Fe_{.15}Mn_{2.85}O_4$/1% K | 0.28 |

It is pointed out that Spinels E and F are comparative examples.

EXAMPLE 2

About 8.8 cc. of the above-prepared spinel C (where x=0.75) was placed into an upflow 304 SS stainless steel reactor (0.51 inch I.D.) and pretreated with a gaseous stream of $H_2$ and (helium, nitrogen) in a 1:9 volume ratio at 100 psig at 500° C. and 600 v/v/hr. (SHSV) for 5.5 hours. Then the pretreated catalyst was contacted with a 1:1 $H_2$:CO feedstream in helium at 300 psig, at 305° C., and a space velocity of 1000 v/v/hr (SHSC) for one or more hours and the products collected and analyzed by gas chromotography versus known standards. The results are listed below in Table III. Unless otherwise indicated, the listed temperatures in the process are furnace temperatures.

A Comparative run was made under substantially the same conditions using a $Fe_3O_4$/1% K catalyst as prepared by the procedure described above in Example (1).

TABLE III

| Catalyst | $Fe_3O_4$/1% K | $Fe_{2.25}Mn_{.75}O_4$/1% K |
|---|---|---|
| Bed Temp (°C.) | 350 | 305 |
| $H_2$/CO feed | 1.0 | 1.0 |
| SHSV (v/v/hr) | 1000 | 1000 |
| Pressure (psig) | 300 | 300 |
| % CO Conversion | 87 | 92 |
| to $CO_2$ | 49 | 44 |
| to HC's | 38 | 48 |
| Wt. % Selectivity ($CO_2$—free basis) | | |
| $CH_4$ | 19.0 | 9.6 |
| $C_2^=$ | 5.7 | 8.6 |
| $C_3^=$ | 15.9 | 14.9 |
| $C_4^=$ | 8.6 | 10.2 |
| $C_5^=$ | 5.0 | 6.0 |
| $C_2^o$-$C_5^o$ | 15.4 | 7.0 |
| $C_6^=$-$C_{20}^=$ | 14.9 | 20.1 |
| $C_6^o$-$C_{20}^=$ | 10.4 | 15.7 |
| $C_{21}^+$ | 5.1 | 7.9 |

As is seen from the data, the Mn-containing spinel catalyst provides greater activity, lower methane and higher $C_2$-$C_5$ alpha-olefin selectivity than the all iron analog.

EXAMPLE 3

Catalyst D, as prepared by the procedure outlined in Example 1, where y=1.0, was promoted with 1 gm.-atom % K as $K_2CO_3$ or $K_2SO_4$. Samples of 8.8 cc of the catalysts were pretreated with $H_2$ at 100 psig, 600 v/v/hr and maintained at 500° C. for 5.5 hr. Then, CO hydrogenation conditions were employed at: 300° C., 1:1 $H_2$/CO, SHSV of 1000 v/v/hr and 300 psig in the tubular upflow 304 SS reactor described in Example 2. Results are provided in Table IV.

TABLE IV

| Performance of $Fe_2MnO_4$/1% K As a Function of Potassium Promoter | | |
|---|---|---|
| Promoter | $K_2CO_3$ | $K_2SO_4$ |
| % CO Conversion | 94.4 | 96.3 |
| to $CO_2$ | 42.0 | 41.0 |

TABLE IV-continued

Performance of $Fe_2MnO_4/1\%$ K
As a Function of Potassium Promoter

| Promoter | $K_2CO_3$ | $K_2SO_4$ |
|---|---|---|
| to HC's | 52.4 | 55.3 |
| Wt. % Selectivity | | |
| $CH_4$ | 7.7 | 6.6 |
| $C_2^=-C_6^=$ | 18.5 | 35.9 |
| $C_2^o-C_6^o$ | 4.8 | 5.6 |
| $C_7^+$ | 69.0 | 51.9 |

Conditions:
300° C., 1:1 $H_2$:CO, 1000 v/v/hr., 300 psig

As seen in the above results, the use of $K_2SO_4$ as a promoter leads to higher selectivity to alpha-olefins. (See also W. L. Van Dijk et al., *Applied Catalysis*, 2 (1982) pp. 273–288).

EXAMPLE 4

Catalysts prepared by the procedure outlined in Example 1, where y=0.15, 0.75, 1.0 and 2.85, with 1% wt. K as $K_2CO_3$ employed as a promoter were pretreated according to the procedure described in Example 2 and then subjected to CO hydrogenation conditions: 270° C., 0.66:1 $H_2$:CO, SHSV of 1000 v/v/hr and 300 psig in the tubular 304 SS upflow reactor described in Example 2 for 12 hours. Results are provided in Table V.

TABLE V

Performance of $Fe_{3-y}Mn_yO_4 1\%$ K
as a Function of Fe:Mn Ratio

| Y = | 0.15 | 0.75 | 1.0 | 2.85 |
|---|---|---|---|---|
| Fe:Mn | 19 | 3 | 2 | 0.05 |
| % CO Conversion | 80.0 | 89.1 | 38.9 | <5.0 |
| to $CO_2$ | 32.0 | 35.0 | 18.9 | NA[a] |
| to HC's | 48.0 | 54.1 | 20.0 | NA |
| Wt. % Select | | | | |
| $CH_4$ | 6.5 | 4.3 | 5.0 | NA |
| $C_2^=-C_6^=$ | 22.8 | 19.2 | 32.2 | NA |
| $C_2^o-C_6^o$ | 4.8 | 3.2 | 7.8 | NA |
| $C_7^+$ | 65.9 | 73.3 | 55.0 | NA |

Conditions:
270° C., 0.66:1 $H_2$:CO, 1000 v/v/hr, 300 psig.
[a]Not available

As seen in the above results, catalysts with an Fe:Mn atomic ratio ≧2.0 give good activity and selectivity to alpha-olefin although catalysts with Fe:Mn≧2.0 exhibit diminished activity relative to more iron rich analogs.

What is claimed is:

1. A process for synthesizing a hydrocarbon mixture containing $C_2$–$C_6$ olefins comprising the step of contacting a catalyst composition comprised of an unsupported iron-manganese spinel: said spinel exhibiting a single spinel phase, being isostructural with $Fe_3O_4$ as determined by X-ray diffractometry, and possessing an iron-manganese atomic ratio of 2:1 to 19:1, said spinel being surface impregnated or deposited with a potassium salt, the atomic ratio of iron/potassium being about 20:1 to 200:1, with a mixture of CO/hydrogen under process conditions of pressure, space velocity (SHSV) and elevated temperature for time sufficient to produce said $C_2$–$C_6$ olefins.

2. The process of claim 1 wherein said hydrogen and CO are present in a $H_2$/CO ratio of about 0.5 to 2.5.

3. The process of claim 1 wherein said temperature is in a range of about 200° to 350° C.

4. The process of claim 1 wherein said pressure is in a range of about 50 to 1000 psig.

5. The process of claim 1 wherein said space velocity is in the range of about 200 to 4000 V/V/hr.

6. The process of claim 1 wherein said spinel is of the formula: $Fe_xMn_yO_4$, wherein x and y are integer or decimal values other than zero, the sum of x+y is 3 and the ratio of x/y is 2:1–19:1.

7. The process of claim 6 wherein the ratio x/y is 3:1 to 7:1.

8. The process of claim 6 wherein said spinel is of the formula: $Fe_{2.85}Mn_{0.15}O_4$, $Fe_{2.625}Mn_{0.375}O_4$, $Fe_{2.25}Mn_{0.75}O_4$, or $Fe_{2.97}Mn_{0.03}O_4$.

9. The process of claim 1 wherein said unsupported catalyst composition is in physical admixture with a diluent material which aids in heat transfer and removal from the catalyst composition during said process.

10. The process of claim 9 wherein said diuent is selected from powdered quartz, porous silica, kieselguhr, talc, powdered borosilicate glass, $TiO_2$, $SiO_2$, $Al_2O_3$, clays, zeolites, MgO, $La_2O_3$, $Cr_2O_3$, $MnO_2$, and the like.

11. The process of claim 1 wherein said promoter agent is potassium carbonate of potassium sulfate.

12. The process of claim 1 wherein said spinel is partially reduced and carbided in situ in the process.

13. The process of claim 1 wherein said product hydrocarbon mixture contains 20 wt. % and above $C_2$–$C_6$ hydrocarbons of the total weight of hydrocarbons produced.

14. The process of claim 13 wherein said $C_2$–$C_6$ hydrocarbons contains $C_2$–$C_6$ olefins in above 50 wt. % of the total $C_2$–$C_6$ hydrocarbons.

15. A process for synthesizing a hydrocarbon mixture containing $C_2$–$C_6$ olefins comprising the step of contacting a partially reduced and carbided catalyst composition comprised of an unsupported iron-manganese spinel of the formula: $Fe_{2.25}Mn_{0.75}O_4/1$ gram-atom % K, as $K_2SO_4$, said spinel exhibiting a single spinel phase, being isostructural with $Fe_3O_4$ as determined by X-ray diffractometry, with a 1:1 mixture of CO/hydrogen under process conditions of 300 psig pressure, 1000 v/v/hr. space velocity (SHSV) and 300° C. temperature for time sufficient to produce said $C_2$–$C_6$ olefins.

* * * * *

UNITED STATES PATENT AND TRADEMARK OFFICE
CERTIFICATE OF CORRECTION

PATENT NO. : 4,670,476

DATED : June 2, 1987

INVENTOR(S) : Stuart L. Soled, et al.

It is certified that error appears in the above-identified patent and that said Letters Patent is hereby corrected as shown below:

On the Title, Item [21]   delete "817,778" insert --817,783-- thereof

Signed and Sealed this

Ninth Day of February, 1988

Attest:

DONALD J. QUIGG

*Attesting Officer*     *Commissioner of Patents and Trademarks*